United States Patent
Hack et al.

(10) Patent No.: US 9,252,420 B2
(45) Date of Patent: Feb. 2, 2016

(54) METHOD AND DEVICE FOR FORMING AN ELECTROLYTE FILM ON AN ELECTRODE SURFACE

(71) Applicant: Airbus Operations GmbH, Hamburg (DE)

(72) Inventors: Theo Hack, München (DE); Siva Palani, Riemerling (DE)

(73) Assignee: Airbus Operations GmbH (DE)

( * ) Notice: Subject to any disclaimer, the term of this patent is extended or adjusted under 35 U.S.C. 154(b) by 4 days.

(21) Appl. No.: 13/918,340

(22) Filed: Jun. 14, 2013

(65) Prior Publication Data

US 2013/0280416 A1    Oct. 24, 2013

Related U.S. Application Data

(63) Continuation of application No. PCT/DE2011/002083, filed on Dec. 7, 2011.

(30) Foreign Application Priority Data

Dec. 17, 2010   (DE) .......................... 10 2010 055 042

(51) Int. Cl.
  *H01M 4/04*    (2006.01)
  *B05B 7/00*    (2006.01)
  (Continued)

(52) U.S. Cl.
  CPC ........... *H01M 4/0407* (2013.01); *B05B 7/0012* (2013.01); *B05B 12/084* (2013.01); *B05B 13/0228* (2013.01); *B05B 17/0615* (2013.01); *G01N 17/02* (2013.01); *B05C 5/02* (2013.01)

(58) Field of Classification Search
  CPC .... B05B 12/084; B05B 17/0623; B05C 5/02; H01M 4/04
  USPC ............... 118/300, 712; 134/17, 37; 204/404, 204/196.06, 275.1; 29/623.1–623.5; 427/115
  See application file for complete search history.

(56) References Cited

U.S. PATENT DOCUMENTS 3,880,112 A  *  4/1975  Spitz et al. .................... 118/323
4,009,462 A  *  2/1977  Bernasconi .................... 338/80

(Continued)

FOREIGN PATENT DOCUMENTS

| DE | 3304648 A1 | 8/1983 |
| EP | 1746408 A1 | 1/2007 |
| GB | 1362803 A | 8/1974 |
| JP | 401290507 A | * 11/1989 |
| JP | 401298168 A | * 12/1989 |

OTHER PUBLICATIONS

O Okada et al: "Behavior of liquid films and droplets in the non-equilibrium region of a downward annular mist flow (comparison of porous and central nozzle mixing methods)", International Journal of Multiphase Flow, vol. 19, Issue 1, Feb. 1, 1993, pp. 79-89, XP55032209, ISSN: 0301-9322, DOI: 10.1016/0301-9322(93)90024-O. (Abstract only.).

(Continued)

*Primary Examiner* — Laura Edwards
(74) *Attorney, Agent, or Firm* — Lerner, David, Littenberg, Krumholz & Mentlik, LLP

(57) ABSTRACT

In a method for forming an electrolyte film on an electrode surface, the liquid electrolyte is sprayed into a cavity to form an electrolyte mist; the electrolyte mist exits the cavity through an opening and then flows across the electrode surface, which is directed downward at an angle behind the opening, whereby an electrolyte film is formed on the electrode surface and wherein the thickness of the electrolyte film is set by means of the angle of inclination of the electrode surface. A corresponding device includes an electrolyte tank communicating with a mist chamber for accommodating sprayed electrolyte by means of a spraying apparatus, wherein the mist chamber comprises a mist outlet. Furthermore, a retainer for fixing the electrode surface at a specifiable angle of inclination is provided, so that electrolyte mist, which can exit through the mist outlet, flows across the electrode surface to form an electrolyte film.

11 Claims, 1 Drawing Sheet

(51) Int. Cl.
  *B05B 12/08* (2006.01)
  *B05B 13/02* (2006.01)
  *B05B 17/06* (2006.01)
  *G01N 17/02* (2006.01)
  *B05C 5/02* (2006.01)

(56) References Cited

U.S. PATENT DOCUMENTS

| | | | |
|---|---|---|---|
| 4,290,384 A | | 9/1981 | Ausschnitt et al. |
| 4,781,941 A | | 11/1988 | Inukai et al. |
| 4,994,159 A | * | 2/1991 | Agarwala et al. ............ 205/776 |
| 5,166,000 A | | 11/1992 | Singh et al. |
| 6,132,653 A | * | 10/2000 | Hunt et al. ........................ 264/5 |
| 2005/0225208 A1 | * | 10/2005 | Yasui et al. .................... 310/328 |

OTHER PUBLICATIONS

Tooru Tsuru et al: "Electrochemical studies on corrosion under a water film", Materials Science and Engineering A, vol. 198, Issues 1-2, Jul. 15, 1995, pp. 161-168, XP55032212, ISSN: 0921-5093, DOI: 10.1016/0921-5093(95)80071-2. (Abstract only.).

O Okada et al: "Behavior of liquid films and droplets in the non-equilibrium region of a downward annular mist flow (comparison of porous and central nozzle mixing methods)", International Journal of Multiphase Flow, vol. 19, Issue 1, Feb. 1, 1993, pp. 79-89, XP55032209, ISSN: 0301-9322, DOI: 10.1016/0301-9322(93)90024-O.

Tooru Tsuru et al: "Electrochemical studies on corrosion under a water film", Materials Science and Engineering A, vol. 198, Issues 1-2, Jul. 15, 1995, pp. 161-168, XP55032212, ISSN: 0921-5093, DOI: 10.1016/0921-5093(95)80071-2.

* cited by examiner

METHOD AND DEVICE FOR FORMING AN ELECTROLYTE FILM ON AN ELECTRODE SURFACE

CROSS-REFERENCE TO RELATED APPLICATIONS

The present application is a continuation of International Application No. PCT/DE2011/002083, filed Dec. 7, 2011, which claims priority from German Patent Application No. 10 2010 055 042.6, filed Dec. 17, 2010, the disclosures of which are incorporated herein by reference.

FIELD OF THE INVENTION

The invention relates to a method and a device for forming an electrolyte film on an electrode surface. Such a method or such a device is used to examine the galvanic corrosion between different metallic materials under different conditions.

BACKGROUND OF THE INVENTION

Atmospheric corrosion phenomena under thin electrolyte films occur predominantly in the interior of aircraft during certain phases of flight or after landing. In this environment the temperature of the outer skin of the fuselage structure is as low as approximately −55° C., so that the components subjected to ambient temperatures cool correspondingly, and on the inside of the structure condensate and ice form, with the result that different metallic materials that are interconnected in an electrically conductive manner are subject to galvanic corrosion in the presence of an aqueous phase.

Up to now galvanic corrosion has been examined in that, for example, the substrate to be examined is cooled to a temperature below the dew point of the electrolyte so that on the substrate an electrolyte film forms that essentially comprises water. This process is associated with a disadvantage in that the film formation cannot be controlled with respect to the conductivity and composition of the electrolyte. After the electrolyte film has formed, uncontrollable and unavoidable evaporation of the film occurs so setting the film thickness is very sensitive to any changes in the ambient conditions, such as the temperature or relative atmospheric humidity. The condensation behavior and the film formation are a function of the thermal conductivity of the substrate or of the substrate combination as well as of the surface texture, and for this reason it is difficult to form a uniform film on a substrate comprising various materials.

In an alternative method the electrolyte film is formed on the substrate in that by means of a pipette a defined quantity of electrolyte that is required for a desired layer thickness is applied which is distributed more or less uniformly on the substrate surface. In this process the uniformity of the layer can only be assumed. Furthermore, as is the case in the above-mentioned method, uncontrollable evaporation effects will occur.

BRIEF SUMMARY OF THE INVENTION

Based on the above, an aspect of the invention provides a generic method and a device that makes it possible on a substrate to form a reproducible electrolyte film comprising a predeterminable film thickness, with this being independent of the substrate material and the electrolyte composition used.

As aspect of the invention allows accurate and reproducible parametric examination of galvanic corrosion, in particular with respect to the film thickness depending on materials and electrolytes to be examined. In this process, in contrast to that of prior art, the film formation is almost independent of the thermal conductivity of the substrate and of the composition of the electrolyte.

The method according to an aspect of the invention is characterized in that
 (a) a liquid electrolyte is atomized into a hollow space to form an electrolyte mist;
 (b) the electrolyte mist issues from the hollow space by way of an opening and subsequently flows over an electrode surface that is aligned behind the opening diagonally downwards,
 (c) as a result of the aforesaid an electrolyte film forms on the electrode surface,
 (d) wherein the thickness of the electrolyte film is set by way of the angle of inclination of the electrode surface.

The device according to an embodiment of the invention is characterized in that it comprises an electrolyte reservoir which by way of an atomizer communicates with a mist chamber for receiving atomized electrolyte, and in that the mist chamber comprises a mist outlet, and furthermore a holder for affixing the electrode surface at a predeterminable angle of inclination is provided so that electrolyte mist that is able to issue from the mist outlet flows over the electrode surface in order to form an electrolyte film.

According to an advantageous embodiment of the invention, the electrolyte is mixed with a nonionic surfactant, preferably 0.05 to 1 vol. % surfactant. This makes it possible to reduce the surface tension between the liquid and the surface, as a result of which the wettability of the substrate and thus the formation of a homogeneous film is improved. Preferably Triton X114 is used as a surfactant.

According to an advantageous embodiment of the invention, the atomizer is designed as a piezo-atomizer. Piezoceramic ultrasonic atomizers are characterized by low energy consumption, low maintenance costs and a long service life, and especially by individually adjustable homogeneous droplet distribution.

According to an advantageous embodiment of the invention, the inclination of the holder is adjustable at an angle to horizontal. Consequently the flow speed of the electrolyte over the substrate, and thus the film thickness, can be set.

According to an advantageous embodiment of the invention, the mist outlet comprises an adjustable opening cross-section. In this manner the quantity of the outflowing electrolyte, and thus, in connection with the inclination of the substrate, the film thickness can be set.

According to an advantageous embodiment of the invention, the aforesaid is housed in a closed chamber. Consequently the influences of the outside temperature and/or atmospheric humidity acting on the film thickness or the corrosion behavior can be minimized.

According to an advantageous embodiment of the invention, the aforesaid comprises an optical acquisition device by means of which the film thickness of the electrolyte film can be measured. In this manner in conjunction with a control device, preferably a computer, by way of the opening of the mist outlet and/or the inclination of the substrate the film thickness can be adjusted or readjusted in an automated manner.

According to an advantageous embodiment of the invention, the optical acquisition device is adjustable with respect to the acquisition point in order to acquire the film thickness at various locations on the electrode surface. In this manner it can be ensured that over the entire substrate, in particular on the two materials, the film thickness is approximately identical, or that the present distribution of the film thickness is known.

According to an advantageous embodiment of the invention, the optical acquisition device is designed as a spectroscope or spectrometer that measures the film thickness by means of optical spectroscopy.

According to an advantageous embodiment of the invention, a controllable fan is arranged in the mist chamber, which fan controls the quantity of electrolyte mist that issues by way of the mist outlet. In this manner the quantity of issuing mist can be controlled better.

According to an advantageous embodiment of the invention, the device described above forms part of apparatus for investigating galvanic corrosion, wherein the substrate comprises two or more surfaces of different materials, which surfaces are arranged so as to be co-planar and form electrodes, and wherein the electrodes can be connected to a current-measuring device by means of connecting lines. In this manner the respective currents between the electrodes can be measured. The connecting lines can also be directly connected to each other when there is no need for measuring the current, because galvanic corrosion between the electrodes requires a conductive connection between the aforesaid.

BRIEF DESCRIPTION OF THE DRAWINGS

Further advantages, characteristics and details are stated in the following description in which an exemplary embodiment is described in detail with reference to the drawing. Described and/or illustrated characteristics per se or in any sensible combination form the subject of the invention, if applicable also independently of the claims. Identical, similar and/or functionally equivalent parts have the same reference characters.

The following are shown in.

DETAILED DESCRIPTION

Figure 1:
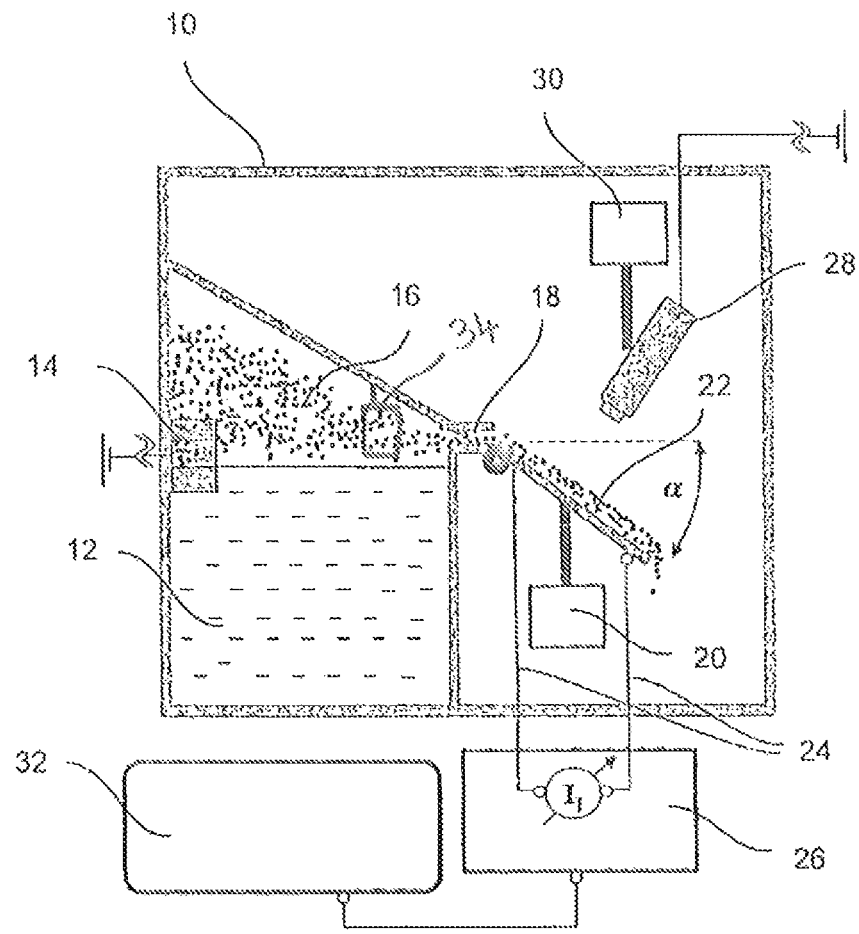
FIG. 1: a device according to an embodiment of the invention.

FIG. 1 shows a hermetically sealable chamber 10 in which an electrolyte reservoir 12 is arranged that contains an electrolyte, for example 0.1 mol/l sodium chloride. An atomizer 14, preferably designed as a piezo-atomizer, is used to atomize electrolyte from the electrolyte reservoir 12 in microdroplets in a size of approximately 0.5-6 μm, which microdroplets collect in the mist chamber 16. The mist chamber 16 comprises a mist outlet 18 that preferably comprises an adjustable cross section in order to control the quantity of the issuing electrolyte mist. In an embodiment, a controllable fan 34 is arranged in the mist chamber, which fan controls the quantity of electrolyte mist that issues by way of the mist outlet. In this manner the quantity of issuing mist can be controlled better.

Furthermore, a substrate holder 20 is provided on which the substrate 22 is affixed, wherein the angle of inclination α of the substrate relative to the horizontal is variable. The substrate 22 is described in more detail in FIG. 2 and comprises at least two co-planar surfaces of different materials, which both act as electrodes. By means of connecting lines 24, all the electrodes are connected to a current-measuring device 26, preferably an ampere meter. The current-measuring device 26 can also comprise switching devices in order to cause a direct connection between electrodes.

Furthermore, the chamber 10 comprises an optical acquisition device 28, preferably a spectroscope or spectrometer, which is adjustable by way of an adjusting device 30 in order to acquire different locations on the substrate 22.

The current-measuring device 26 is coupled to a control device 32 in order to control the arrangement or to acquire and evaluate the measured current. By way of lines (not shown), the optical acquisition device 28 and its adjustment device 30, the atomizer 14, the substrate holder 20 and the cross-sectional adjustment of the mist outlet 18 are also coupled to the control device 32.

Figure 2:
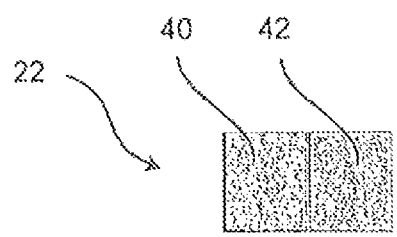
FIG. 2: a substrate comprising two electrodes.

FIG. 2 shows a view of the substrate 22 that comprises two different co-planar electrodes 40, 42 that are arranged side by side, for example carbon-fiber-reinforced plastic and aluminum. The substrate 22 can also comprise more than two electrodes, in particular three or four, which are then in each case connected to the current-measuring device 26 by way of connecting lines 24.

In operation, an electrolyte to be examined is prepared and filled into the electrolyte reservoir 12. Preferably, a nonionic surfactant is added to the electrolyte in order to reduce the surface tension between the liquid and the surface to be wetted, thus facilitating the wettability of the substrate and making it possible for an electrolyte layer that is as homogeneous as possible to form. By means of the atomizer 14 the electrolyte is atomized into the mist chamber 16. The electrolyte mist flows from the mist chamber 16 through the mist outlet 18 and subsequently over the inclined substrate 22, wherein the flow rate is set by way of adjustment of the opening cross section of the mist outlet 18. The continuous flow of mist over the inclined substrate 22 generates an electrolyte film, which is constant after some time, on the substrate, of a film thickness that is predetermined by the inclination of the substrate 22. The electrolyte is then in a state of equilibrium with the continuously flowing flow of mist, which thus, contrary to the situation in prior art, is not exposed to the ambient atmosphere. In this manner, evaporation of the electrolyte film can be prevented. By way of changing the angle of inclination of the substrate, the film thickness can be adjusted within a wide range between 0 and 90 μm. In this arrangement the film thickness is determined by means of the spectrometer 28 that is adjusted by means of the adjusting device 30 in order to determine the film thickness at various locations of the substrate 22. If the film thickness differs from the desired values, by means of the control device 32 the cross section of the mist outlet 18 or the angle of inclination of the substrate 22 can be varied. The angle of inclination α will preferably be in the range of 0° to 90°.

By means of the chamber 10, constant conditions (temperature, convection) are ensured in the interior of said chamber 10 in order to ensure the accuracy and reproducibility of the test procedure.

The invention claimed is:

1. A method for forming an electrolyte film on an electrode surface, comprising:
   atomizing, by an atomizer, a liquid electrolyte contained in an electrolyte reservoir enclosed by a mist chamber into the mist chamber located above the electrolyte reservoir to create an electrolyte mist, the atomizer being configured to provide communication between the electrolyte reservoir and the mist chamber, wherein the electrolyte reservoir, the mist chamber, and the chamber containing the electrode surface are housed within a closed chamber;
   issuing the electrolyte mist from the mist chamber by way of a mist outlet and subsequently flowing over the electrode surface aligned behind the opening diagonally downwards and affixed at a predeterminable angle of inclination by a holder; and as a result of the aforesaid, forming an electrolyte film on the electrode surface, wherein the thickness of the electrolyte film is set by the angle of inclination of the electrode surface.

2. The method of claim 1, wherein the electrolyte is mixed with a nonionic surfactant, preferably 0.1 to 1 vol. % surfactant.

3. A device for forming an electrolyte film on an electrode surface, said device comprising an electrolyte reservoir;

a mist chamber for receiving atomized electrolyte and comprising a mist outlet, wherein the mist chamber is located above the electrolyte reservoir enclosed by the mist chamber;

an atomizer configured to provide communication between the electrolyte reservoir and the mist chamber;

a chamber containing the electrode surface and in fluid connection with the mist chamber via the mist outlet, wherein the electrolyte reservoir, the mist chamber, and the chamber containing the electrode surface are housed within a closed chamber; and a holder for affixing the electrode surface at a predeterminable angle of inclination, wherein electrolyte mist issuing from the mist outlet is configured to flow over the electrode surface, thereby forming electrolyte film thereupon.

4. The device of claim 3, wherein the atomizer is configured as a piezo-atomizer.

5. The device of claim 3, wherein the inclination of the holder is adjustable at an angle of between 0° and 90° to horizontal.

6. The device of claim 3, wherein the mist outlet comprises a variable opening cross section.

7. The device of claim 3, further comprising an optical acquisition device for measuring the film thickness of the electrolyte film.

8. The device of claim 7, wherein the optical acquisition device is adjustable in order to acquire film thickness at various locations of the electrode surface.

9. The device of claim 7, wherein the optical acquisition device is configured as a spectroscope or spectrometer for measuring the film thickness by optical spectroscopy.

10. The device of claim 3, further comprising a controllable fan arranged in the mist chamber, wherein the fan is configured to control the quantity of electrolyte mist issuing by way of the mist outlet.

11. An apparatus for investigating galvanic corrosion, comprising a device for forming an electrolyte film on an electrode surface comprising:

an electrolyte reservoir;

a mist chamber for receiving atomized electrolyte and comprising a mist outlet, wherein the mist chamber is located above the electrolyte reservoir enclosed by the mist chamber;

an atomizer configured to provide communication between the electrolyte reservoir and the mist chamber;

a chamber containing the electrode surface and in fluid connection with the mist chamber via the mist outlet, wherein the electrolyte reservoir, the mist chamber, and the chamber containing the electrode surface are housed within a closed chamber; and a holder for affixing the electrode surface at a predeterminable angle of inclination, wherein electrolyte mist issuing from the mist outlet is configured to flow over the electrode surface, thereby forming an electrolyte film thereupon, wherein the electrode surface comprises two or more surfaces of different materials and arranged in a coplanar manner, which surfaces in each case form electrodes, and wherein the electrodes are configured to be connected to a current-measuring device by connecting lines.

* * * * *